(12) United States Patent
Johnson et al.

(10) Patent No.: US 11,460,410 B2
(45) Date of Patent: Oct. 4, 2022

(54) BIOINDICATOR COMPONENT APPLIED TO AN ARTICLE

(71) Applicant: PUMA SE, Herzogenaurach (DE)

(72) Inventors: Charles Johnson, Nuremberg (DE); Matthias Hartmann, Forchheim (DE)

(73) Assignee: PUMA SE, Herzogenaurach (DE)

( * ) Notice: Subject to any disclaimer, the term of this patent is extended or adjusted under 35 U.S.C. 154(b) by 771 days.

(21) Appl. No.: 16/378,431

(22) Filed: Apr. 8, 2019

(65) Prior Publication Data

US 2020/0319113 A1 Oct. 8, 2020

(51) Int. Cl.
| | |
|---|---|
| *G01N 21/00* | (2006.01) |
| *G01N 21/78* | (2006.01) |
| *G01N 33/00* | (2006.01) |
| *A41B 9/06* | (2006.01) |
| *A41D 1/00* | (2018.01) |
| *A43B 7/00* | (2006.01) |

(52) U.S. Cl.
CPC ......... *G01N 21/783* (2013.01); *G01N 33/004* (2013.01); *A41B 9/06* (2013.01); *A41D 1/002* (2013.01); *A41D 2600/10* (2013.01); *A43B 7/00* (2013.01)

(58) Field of Classification Search
CPC ............... G01N 21/783; G01N 33/004; G01N 2333/405; G01N 33/52; A41D 1/002; A41D 2600/10; A41B 9/06; A43B 7/00; Y02A 50/20
See application file for complete search history.

(56) References Cited

U.S. PATENT DOCUMENTS

| | | | |
|---|---|---|---|
| 2,240,599 | A | 5/1941 | Amberg |
| 4,063,371 | A | 12/1977 | Batra |
| 4,092,221 | A | 5/1978 | Schlichting, Jr. |
| 6,376,213 | B1 | 4/2002 | Oda et al. |
| 8,741,597 | B2 | 6/2014 | Orenga et al. |
| 8,745,892 | B2 | 6/2014 | Moretti |
| 2003/0199095 | A1 | 10/2003 | Yuyama et al. |
| 2005/0031733 | A1 | 2/2005 | Domingues et al. |

(Continued)

FOREIGN PATENT DOCUMENTS

| | | |
|---|---|---|
| WO | 2010006442 A1 | 1/2010 |
| WO | 2020074109 A1 | 4/2020 |

OTHER PUBLICATIONS

International Preliminary Report on Patentability (Form IPEA/409) of International Application No. PCT/EP2018/077968, dated Feb. 22, 2021, 19 pages.

(Continued)

*Primary Examiner* — Ojiako K Nwugo
(74) *Attorney, Agent, or Firm* — Quarles & Brady LLP

(57) ABSTRACT

A bioindicator assembly for determining a level of $CO_2$ in a surrounding environment includes an article and a bioindicator component applied to the article. The bioindicator component includes a composite fabric that has a substrate, wherein a biodegradable material is applied to the substrate, a membrane that is coupled with the composite fabric to define an interior cavity, the membrane being semi-permeable, a bioindicator that changes color, form, shape, or texture when exposed to $CO_2$, and an attachment mechanism coupled to a rear side of the composite fabric.

20 Claims, 12 Drawing Sheets

(56) References Cited

U.S. PATENT DOCUMENTS

| | | | |
|---|---|---|---|
| 2005/0204449 A1 | 9/2005 | Baron et al. | |
| 2006/0257908 A1 | 11/2006 | Rui et al. | |
| 2013/0130399 A1* | 5/2013 | Mills | G01N 31/224 |
| | | | 206/459.1 |
| 2013/0269592 A1* | 10/2013 | Heacock | A61M 5/5086 |
| | | | 116/206 |
| 2014/0065311 A1 | 3/2014 | Moseley et al. | |
| 2015/0346513 A1* | 12/2015 | Heacock | G02C 7/049 |
| | | | 351/159.3 |
| 2015/0370320 A1* | 12/2015 | Connor | A61B 5/1121 |
| | | | 345/173 |
| 2016/0135543 A1 | 5/2016 | Anceresi et al. | |
| 2017/0027482 A1* | 2/2017 | Zilberstein | A61B 5/082 |
| 2017/0066583 A1 | 3/2017 | Kimbrough | |
| 2017/0082573 A1* | 3/2017 | Vingerhoets | G01N 27/416 |
| 2017/0169692 A1* | 6/2017 | Parra | G08B 21/14 |
| 2017/0322163 A1* | 11/2017 | Heacock | G01N 21/78 |
| 2018/0104017 A1* | 4/2018 | Heacock | G01N 31/223 |
| 2019/0145849 A1* | 5/2019 | Jensen | G01N 33/004 |
| | | | 340/984 |
| 2019/0285577 A1* | 9/2019 | Swager | G01N 33/004 |
| 2020/0113287 A1 | 4/2020 | Johnson et al. | |
| 2020/0156839 A1 | 5/2020 | Abramov | |

OTHER PUBLICATIONS

Anonymus: "Puma Biodesign: Breathing Shoes", , Apr. 17, 2018 (Apr. 17, 2018), Retrieved from the Internet: URL:https://vimeo.com/265128805 [retrieved on Jun. 15, 2020].

Anna Winston: "Puma and MIT Design Lab envision a future of selfadapting, per-media-lab-puma-future-s", May 24, 2018 (May 24, 2018), XP055594193, Retrieved from the Internet: URL:https://www.dezeen.com/2018/05/24/mit-media-lab-pumafuture-sportsweardesign/ [retrieved on Jun. 5, 2019].

Shah Aamer Ali et al: "Microbial degradation of aliphatic and aliphatic-aromatic co-polyesters", Applied Microbiology and Biotechnology, Springer Berlin Heidelberg, Berlin/Heidelber vol. 98, No. 8, Feb. 13, 2014 (Feb. 13, 2014), pp. 3437-3447, XP035328980, ISSN: 0175-7598, DOI: 10.1007/S00253-014-5558-1 [retrieved on Feb. 13, 2014].

International Search Report and Written Opinion issued in corresponding International Application No. PCT/IB2020/053028, dated Jun. 29, 2020, 15 pages.

International Search Report and Written Opinion issued in corresponding International Application No. PCT/EP2018/077968, dated Jun. 13, 2019, 11 pages.

Shah et al., "Degradation of polyurethane by novel bacterial consortium isolated from soil," Annals of Microbiology, 58 (3):381-386 (2008).

Yoshida et al., "A bacterium that degrades and assimilates poly-(ethylene terephalate)," Science, Mar. 11, 2016, 351 (6278):1196-1199.

International Search Report and Written Opinion of the International Searching Authority from corresponding PCT Application No. PCT/IB2020/053031, dated Aug. 28, 2020 (11 pages).

Nigam, P. S. (Aug. 23, 2013). Microbial enzymes with special characteristics for biotechnological applications. Biomolecules. Retrieved Feb. 1, 2022, from https://www.ncbi.nlni.nih.gov/pmc/articles/PMC4030947/ (Year: 2013).

Jerry, D. C. T., Mohammed, T., & Mohammed, A. (2017). Yeast-generated CO2: A convenient source of carbon dioxide for Mosquito trapping using the BG-sentinel® traps. Asian Pacific Journal of Tropical Biomedicine. Retrieved Feb. 1, 2022, from https://www.sciencedirect.com/science/article/pii/S2 (Year: 2017).

Hedge et al. "A comparative review of footwear-based wearable systems", Electronics, 2016, vol. 5, issue 3, 48 (Year: 2016).

Catenacci, T., "These new shoes designed by Puma and MIT Lab can tell how you're feeling", CNBC news article, published Jun. 6, 2018, https://www.cnbc.com/2018/06/05/puma-mit-shoes-can-breathe.htlml (Year: 2018).

Low, JH et al. "A pressure-redistributing insole using solft sensors and actuators", 2015 IEEE International Conference on Robotics and Automation (ICRA), 2015, pp. 2926-2930. (Year: 2015).

* cited by examiner

BIOINDICATOR COMPONENT APPLIED TO AN ARTICLE

CROSS REFERENCE TO RELATED APPLICATIONS

Not applicable

REFERENCE REGARDING FEDERALLY SPONSORED RESEARCH OR DEVELOPMENT

Not applicable

SEQUENCE LISTING

Not applicable

BACKGROUND

1. Field of the Disclosure

The present disclosure relates generally to a bioindicator component that can be applied to an article, such as an article of clothing. More specifically, the present disclosure relates to a bioindicator component that reacts and adapts to the environment around the wearer based on one or more sensed changes in one or more concentrations of atmospheric surroundings.

2. Description of the Background

Many consumers desire informational feedback from a device during a workout or when engaging in physical activities. Typically, such feedback comes from one or more electronic devices such as cell phones, watches, fitness trackers, or other portable electronic devices. This feedback may provide information related to a heart rate, a sleep cycle, a distance traveled, or other types of feedback that such devices can track and display. In many instances, this type of feedback can assist a user in tracking or monitoring one or more data points for ensuring that a user has achieved a desired amount of exercise or sleep, or a desired heart rate during certain periods of time. Many presently-available feedback systems require an electronic assembly connected to one or more sensors that obtain sensed information, and send signals indicative of the sensed information to a controller where the information can be synthesized and output to a user.

While certain information is readily obtainable by one or more sensors, such as an accelerometer, which is connected to an electronic device, a significant amount of desirable information cannot simply be captured by cost-effective sensors and transmitted to an electronic device. For example, few if any electronic devices are capable of obtaining and displaying real-time temperature or pressure information, due to a number of factors associated with obtaining and displaying correct information to a user.

Further, few if any electronic devices are capable of obtaining information related to atmospheric conditions that can include ozone levels, $CO_2$ levels, or particulate matter levels, among other desirable environmental information. Some limitations with obtaining and displaying such information lie in an inability to include these types of sensors in compact electronic devices that the consuming public has become accustomed to. Further, cost considerations may prevent electronic device manufacturers from including such sensors.

While electronic devices may be able to effectively and efficiently obtain and display information related to current atmospheric conditions, an alternative need exists for an effective, useful tool to readily determine certain atmospheric conditions related to the surrounding atmosphere. More specifically, a need exists for an easy and efficient way for a user to determine whether the surrounding atmosphere is suitable for physical activities.

SUMMARY

A bioindicator component, as described herein, may have various configurations, and is generally attachable to and detachable from an exterior surface of an article, such as an article of clothing or footwear. However, in some embodiments, the bioindicator component is permanently applied to an article, and includes a peelable or removable impermeable layer removable therefrom.

In some embodiments, a bioindicator component for determining a level of $CO_2$ in a surrounding environment includes a composite fabric that includes a substrate, wherein a biodegradable material is applied to the substrate. The bioindicator component further includes a membrane that is coupled with the composite fabric to define an interior cavity, the membrane being semi-permeable, a bioindicator that changes color, form, shape, or texture when exposed to $CO_2$, and an attachment mechanism coupled to a rear side of the composite fabric.

In some embodiments, the substrate is in the shape of a circle. In some embodiments, the attachment mechanism comprises hooks. In some embodiments, the bioindicator changes color when exposed to $CO_2$. In some embodiments, the bioindicator includes an algae. In some embodiments, the algae is of the type oscillatoria. In some embodiments, when the bioindicator is exposed to a threshold level of $CO_2$, the bioindicator component turns purple.

In some embodiments, a bioindicator assembly for determining a level of $CO_2$ in a surrounding environment includes an article and a bioindicator component applied to the article. The bioindicator component comprises a composite fabric that includes a substrate, wherein a biodegradable material is applied to the substrate, a membrane that is coupled with the composite fabric to define an interior cavity, the membrane being semi-permeable, a bioindicator that changes color, form, shape, or texture when exposed to $CO_2$, and an attachment mechanism coupled to a side of the composite fabric.

In some embodiments, the article is an article of clothing. In some embodiments, the article is an article of footwear. In some embodiments, the bioindicator comprises an algae that changes color when exposed to $CO_2$. In some embodiments, the algae is of the type oscillatoria. In some embodiments, when the bioindicator component is exposed to a threshold level of $CO_2$, the bioindicator component turns a different color.

In some embodiments, a method of utilizing a bioindicator assembly that can determine a threshold level of $CO_2$ in a surrounding environment includes the step of removing a bioindicator component from a pouch. The bioindicator component comprises a composite fabric that includes a substrate, wherein a biodegradable material is applied to the substrate, a membrane that is coupled with the composite fabric to define an interior cavity, the membrane being semi-permeable, a bioindicator that changes color, form, shape, or texture when exposed to $CO_2$, and an attachment mechanism coupled to a rear side of the composite fabric. The method further includes the steps of applying the bioindicator component to an article via the attachment mechanism along the bioindicator component, transferring the bioindicator component from a first environment to a second environment, wherein a $CO_2$ level is greater in the second environment than the first environment, and placing the bioindicator component into the pouch.

In some embodiments, the article is an article clothing. In some embodiments, the article is an article of footwear. In some embodiments, the bioindicator comprises an algae that changes color when exposed to $CO_2$. In some embodiments, the algae is of the type oscillatoria. In some embodiments, when the bioindicator component is exposed to a threshold level of $CO_2$, the bioindicator component turns a different color. In some embodiments, the attachment mechanism comprises a hook and loop structure.

Other aspects of the article of clothing, including features and advantages thereof, will become apparent to one of ordinary skill in the art upon examination of the figures and detailed description herein. Therefore, all such aspects of the article of footwear are intended to be included in the detailed description and this summary.

DETAILED DESCRIPTION OF THE DRAWINGS

Figure 1:
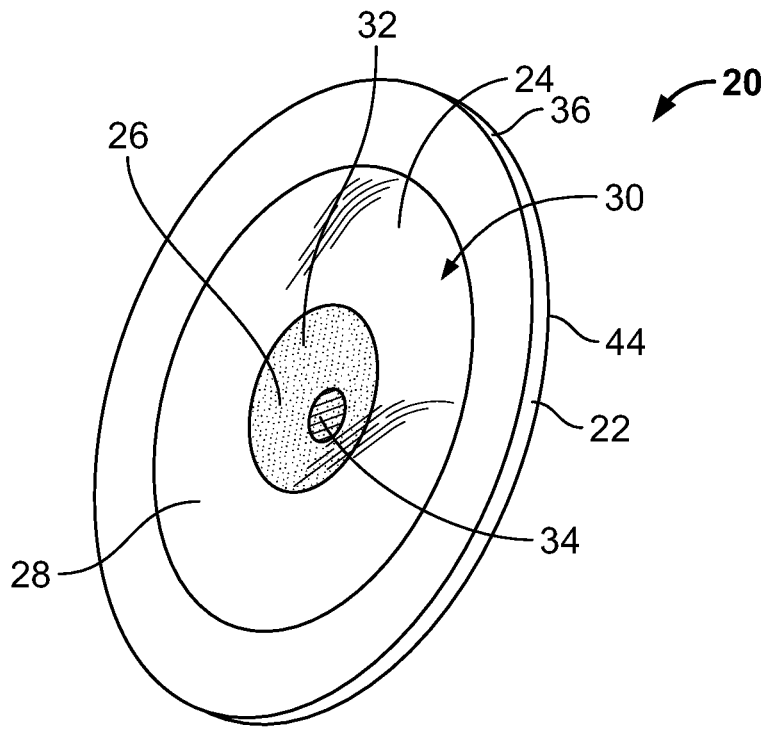
FIG. 1 is a front isometric view of a bioindicator component in accordance with the present disclosure.

The following discussion and accompanying figures disclose various embodiments or configurations of a bioindicator component that is applied to or integral with an article of clothing or another article. Although embodiments of a bioindicator component are disclosed that are attachable to and detachable from an article, such as an article of clothing, e.g., a shirt, concepts associated with embodiments of the bioindicator component may be applied to a wide range of athletic clothing articles, including shorts, socks, underwear, jackets, or leggings, for example. Concepts of the bioindicator component may also be applied to articles of clothing that are considered non-athletic, including sports coats, dresses, tuxedos, etc. In addition to clothing, particular concepts described herein may also be applied and incorporated in other types of apparel or other athletic equipment, including footwear, shoes, helmets, padding or protective pads, shin guards, and gloves. Even further, particular concepts described herein may be incorporated in cushions, backpack straps, golf clubs, or other consumer or industrial products. Accordingly, concepts described herein may be utilized in a variety of products.

The term "about," as used herein, refers to variation in the numerical quantity that may occur, for example, through typical measuring and manufacturing procedures used for articles of clothing or footwear, or other articles of manufacture that may include embodiments of the disclosure herein; through inadvertent error in these procedures; through differences in the manufacture, source, or purity of the ingredients used to make the compositions or mixtures or carry out the methods; and the like. Throughout the disclosure, the terms "about" and "approximately" refer to a range of values ±5% of the numeric value that the term precedes.

The terms "weight percent," "wt-%," "percent by weight," "% by weight," and variations thereof, as used herein, refer to the concentration of a substance or component as the weight of that substance or component divided by the total weight, for example, of the composition or of a particular component of the composition, and multiplied by 100. It is understood that, as used herein, "percent," "%," and the like may be synonymous with "weight percent" and "wt-%."

The term "bioindicator" and variations thereof, as used herein, refers to a composition comprising a microorganism, which changes color, shape, form, or texture in reaction to a stimulant or stimuli. The microorganism selected for use in the bioindicator has one or more beneficial properties that make it responsive to the stimulant or stimuli in the environment.

A stimulant or stimuli may be used to prompt, accelerate, or decelerate degradation. For example, in some aspects, the stimuli used to prompt or accelerate degradation or biodegradation may include, but are not limited to, variations in temperature (such as increases or decreases in heat), light, UV light, a change in pressure, a change in humidity, a change in pH, exposure to a liquid (e.g., water, salt water, an acidic solution, a basic solution), exposure to a gas (e.g., $CO_2$, $NH_3$, $NO_2$, $O_2$), or a solvent.

The stimulant may prompt, accelerate, or deaccelerate change to the bioindicator after a single exposure by one or more stimulants, or the bioindicator may be tuned to respond after repeated exposure to the stimulant or stimuli. In some aspects, the stimulant may be an environmental stimulant such as exposure to one or more natural elements including humidity or pressure and the degradation may be tuned to respond to an environmental stimulant after a particular threshold is reached or period of time has elapsed. In yet another aspect, the stimulant or stimuli may include a variation in temperature and the bioindicator may be tuned to respond to the temperature or change in temperature after a particular threshold is reached or a period of time has elapsed. In still another aspect, the stimulant may be light of a given wavelength, such as UV light, visible light, or infrared radiation, or it may be a broad spectrum of light, and the bioindicator may be tuned to respond to the light after a particular threshold is reached or a period of time has elapsed. In some embodiments, the stimulant or stimuli may include $CO_2$, $NO_2$, oxygen, particulate matter, or ozone. In a preferred embodiment, the stimulant is $CO_2$, which may be a proxy for other high levels of pollutants, such as particulate matter.

In some embodiments, the microorganisms detect and/or respond to $CO_2$ through photosynthesis, which requires certain amounts of light and water, and through metabolic pathways that assimilate $CO_2$ and turn it into another compound. The response to $CO_2$ depends on whether the microorganism is photosynthetic or is metabolizing the $CO_2$. In some aspects, the bioindicator includes a photosynthetic microorganism that responds to changes in $CO_2$ concentration.

The microorganism may be a bacteria, an actinobacteria, a proteobacteria, a bacteroidetes, a fungi, a yeast, an algae, or a protozoa. Suitable microorganisms for use in the bioindicator described herein are known and used in the art. For example, the microorganism(s) may be, but is/are not limited to, *Oscillatoria* (e.g., *Oscillatoria rubescens*), *Trichodesmium* (e.g. *Trichodesmium erythraceum*), *Hammatoidea, Heterohormogonium, Scytonema, Gleocapsa, Pleurocapsa, Albrightia, Scytonematopsis, Thalopophila, Myxocarcina, Colteronema, Phormidium corallactinium, Chlamydomonas reinhardtii, Planktothrix rubescens*, and/or *Synechococcus*.

In some embodiments, the microorganism used in the bioindicator may be a recombinant microorganism genetically engineered to express one or more proteins, enzymes, or genes from a microorganism known to express a pigment of interest or to change a color of the microorganism. The bioindicator described herein includes a microorganism in any medium suitable for survival and growth of the microorganism. The medium may be in any form, including a gel, a hydrogel, a liquid, a cream, an oil, a foam, a paste, a powder, and/or a film. Components of the medium may include agar, agarose, peptone, polypeptone, glucose, yeast extract, malt extract, polyethylene glycol, salts, buffers, water, solvents, and/or combinations thereof. In some embodiments, the medium and the microorganism are unrestrained within the bioindicator and can flow freely and change positions. In some embodiments, the medium and/or the microorganism are in a fixed position.

The timing and/or duration of a color change of the bioindicator may be tuned or controlled. For example, one or more additives may be added to the medium or bioindicator composition to tune the response of the microorganism. Additives may also be added to alter a change in color or to make the microorganism more or less responsive to the stimuli. The additive may be a pigment or a dye.

In some embodiments, the microorganism may be introduced into the bioindicator as a biofilm. In some embodiments, the bioindicator may comprise a biofilm. As used herein, the term "biofilm" refers to a film-like layer of bacteria or fungi formed by assembly of a matrix of extracellular polymeric substances which promote cell-to-cell adhesion of bacteria or fungi. The biofilm promotes cell adsorption onto a surface, such as the surface of a polymer or material to be degraded. The biofilm may be introduced into the bioindicator on its own or it may be introduced with a medium that promotes growth and survival of the microorganism as well as maintenance of the biofilm. In some embodiments, one or more dyes may be added to the biofilm to visualize biofilm formation and growth and/or to color the biofilm for use in the bioindicator.

Environmental stimuli that prompt a change of color in the bioindicator may include light, UV light, a change in pressure, a change in humidity, a change in pH, water, or $CO_2$. The stimulant may prompt color change of the bioindicator after a single exposure to the stimulant, or by repeated exposure to the stimulant. Alternatively, the color change may be tuned to respond after a single exposure or repeated exposure to two or more stimuli. The stimulant may be a light of a given wavelength, such as UV light, visible light, or infrared radiation, or it may be a broad spectrum of light, and the color change of the bioindicator may be tuned to respond to the light after a particular threshold is reached or a period of time has elapsed.

In some embodiments, the stimulant is $CO_2$ and the color change is responsive to the level of $CO_2$ encountered by the user. In some embodiments, the bioindicator may be used at a temperature between about 0° C. and about 85° C., e.g., about 0° C., about 5° C., about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., or about 85° C. In some embodiments, the bioindicator may be used at a humidity between about 20% relative humidity and about 100% relative humidity, e.g., about 20%, about 25%, about 30%, about 35%, about 40%, about 45%, about 50%, about 55%, about 60%, about 65%, about 70%, about 75%, about 80%, about 85%, about 90%, about 95%, or about 100%. In some embodiments, the bioindicator is less active or completely inactivated at temperatures below about 30° C., below about 25° C., below about 20° C., below about 15° C., below about 10° C., below about 5° C., or below about 0° C. In some embodiments, the bioindicator is less active or completely inactivated at a humidity of below about 20%, below about 15%, below about 10%, below about 5%, or below about 2%.

Figure 2:
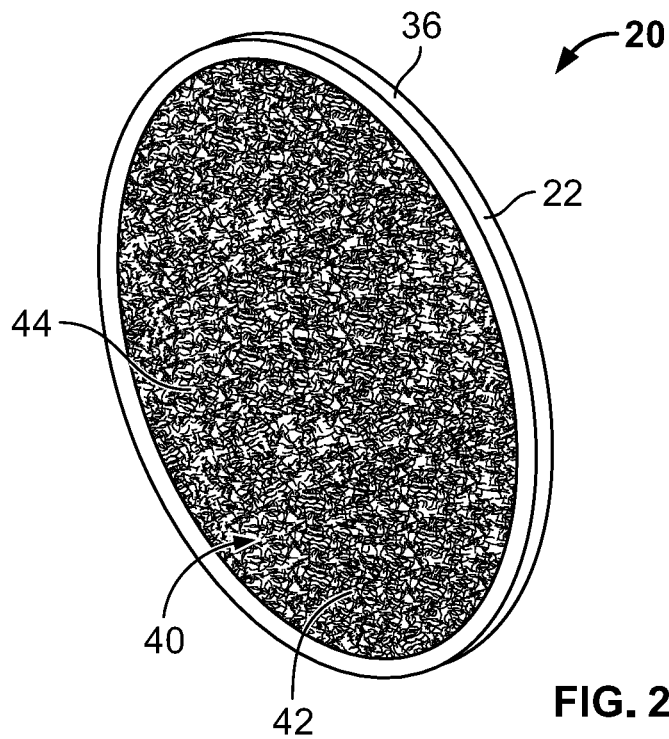
FIG. 2 is a rear isometric view of the bioindicator component of FIG. 1.
Figure 3:
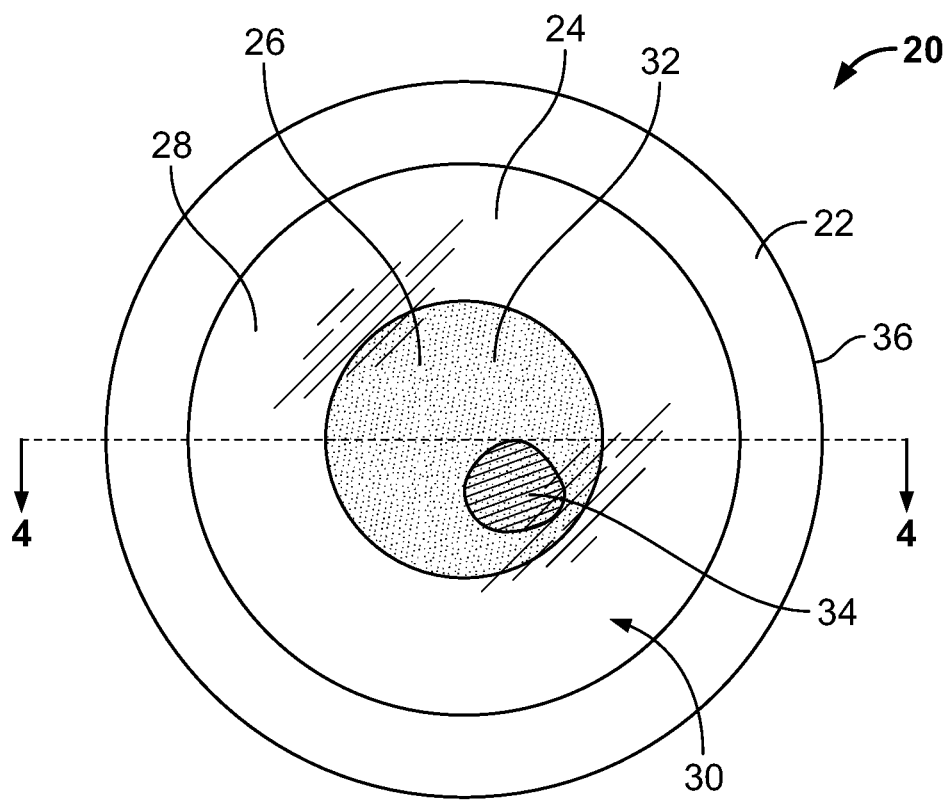
FIG. 3 is a top view of the bioindicator component of FIG. 1.

FIGS. 1-3 depict one embodiment of a bioindicator component 20 in accordance with the present disclosure. The bioindicator component 20 comprises a composite material, and includes a composite fabric 22 and a membrane 24. The membrane 24 may be a type of biological or synthetic polymeric membrane that allows certain molecules or ions to pass through it. In some embodiments, the membrane 24 includes silica, zeolites, metal-organic frameworks, and/or perovskites, which may be used because of strong thermal and chemical resistance as well as high tunability (ability to be modified and functionalized), which can lead to increased permeability and selectivity. The membrane 24 may be used for separating gas mixtures by acting as a permeable barrier through which one or more compounds can move across at different rates or not move at all.

The membrane 24 may also include other types of materials, such as gas permeable polymers. To that end, the membrane 24 may be gas permeable, and may be constructed to allow the stimulant or stimuli, as discussed above, to diffuse through the membrane 24, but prevent other types of material from diffusing or otherwise passing through the membrane 24. The membrane 24 can be tuned such that gas molecules can penetrate according to the molecule size, diffusivity, and/or solubility. The membrane 24 may comprise a net or a perforated foil, which may prevent bioindicator material 26 from escaping through an outer surface 28 of the membrane 24, but allows surrounding environmental gases to contact the bioindicator material 26. It is also anticipated that the membrane 24 will comprise a two-way diffusible gas permeable layer. In some embodiments, the bioindicator material 26 may change color or form in response to an environmental condition, such as a level of ambient gas or particulate matter that is above an identified threshold.

In some embodiments, the membrane 24 may comprise thin film composite (TFC) membranes, which may comprise a high molecular weight amorphous poly(ethylene oxide)/poly(ether-block-amide) (HMA-PEO/Pebax® 2533) layer and/or a highly permeable polydimethylsiloxane (PDMS) intermediate layer which may be pre-coated onto a polyacrylonitrile (PAN) microporous substrate. In some embodiments, it may be advantageous to include TFC membranes that show higher permeable characteristics. In still further embodiments, the membrane 24 may include polyimides, thermally rearranged polymers (TRs), substituted polyacetylenes, polymers with intrinsic microporosity (PIM), and/or polyethers. In some embodiments, it may be advantageous to select a material having tailored macro- and/or microstructures and targeted surface properties.

Still referring to FIGS. 1-3, the composite fabric 22 may be a composite material that includes a biodegradable material (not shown) applied to the composite fabric 22. In some embodiments the biodegradable material may be applied or bonded to the composite fabric 22 in a pattern and, in particular, a pattern of small patches. In some embodiments, two or more of the bioindicator components 20 may be included, which may comprise the same bioindicator material 26 therein, or may include different bioindicators. The bioindicator material 26 may also be disposed in alternative arrangements, and need not be limited to the shape of a circle, as depicted in FIGS. 1-3.

Referring specifically to FIG. 1, a front isometric view of the bioindicator component 20 is shown. The bioindicator component 20 includes the composite fabric 22, which may comprise silicon, and the membrane 24. The membrane 24 and the composite fabric 22, when combined, define an interior cavity 30 within which the bioindicator material 26 is disposed. As noted above, the membrane 24 is semi-permeable, so as to allow gas to enter and leave the interior cavity 30, but prevent fluid or the bioindicator material 26 from exiting the interior cavity 30. The bioindicator material 26 may include a first portion 32 having a higher concentration of bio material and a second portion 34 having a lower concentration of bioindicator material 26, or vice versa. In some embodiments, the first portion 32 includes bioindicator material, while the second portion 34 includes the biodegradable material, as described above, or vice versa. In some embodiments, the first portion 32 includes the bioindicator material 26, while the second portion 34 includes another substance, such as an additive, as outlined above.

Still referring to FIG. 1, the bioindicator component 20 comprises an outer edge 36, which defines a periphery of the bioindicator component 20. In the present embodiment, the bioindicator component 20 is in the shape of a circle, which can be advantageous to allow for a plethora of applications outside of being applied to a shirt or other type of article of clothing. Further, the circular form of the bioindicator component 20 can allow for placement versatility so that the bioindicator component 20 can be used in or applied to other wearables and/or shoes. In alternative embodiments, the outer edge 36 of the bioindicator component 20 is in the shape of an oval, an ellipse, a triangle, a rectangle, a square, a pentagon, a hexagon, an octagon, or another type of polygon.

Referring to FIG. 2, a rear isometric view of the bioindicator component 20 is shown. The outer edge 36 is shown in the figure, along with an attachment mechanism 40, which in the present embodiment includes a plurality of hooks 42, which may be components of a hook and loop structure, e.g., Velcro®. The attachment mechanism 40 allows the bioindicator component 20 to be easily attached to and/or removed from an article of clothing. In some embodiments, the attachment mechanism 40 may include adhesive, magnets, straps, or one or more fasteners. In some embodiments, the attachment mechanism 40 may include a lock and key feature that allows the bioindicator component 20 to be slidingly or fittingly engaged with another component. In some embodiments, an outer flange is provided along the outer periphery of the bioindicator component 20. In some embodiments, the bioindicator component 20 is fixedly attached to the article of clothing.

Figure 4:
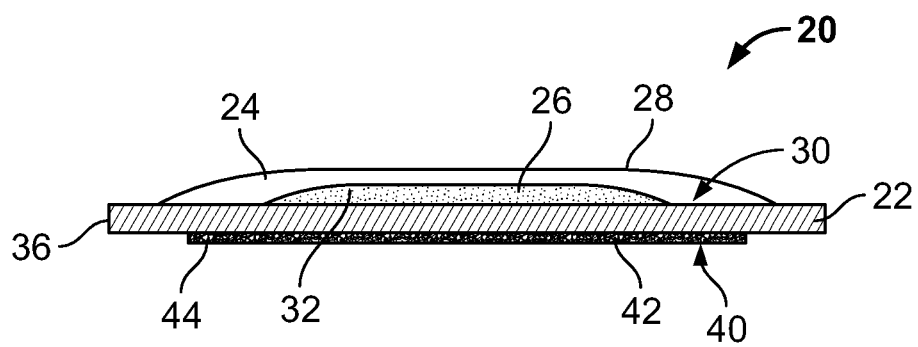
FIG. 4 is a side-cross sectional view taken through line 4-4 of the bioindicator component of FIG. 3.

Now referring to FIG. 3, a top view of the bioindicator component 20 is shown. The circular profile of the bioindicator component 20 is clearly shown in this view, with the first portion 32 and the second portion 34 being more apparent. Referring to FIG. 4, a side-cross sectional view taken through line 4-4 of FIG. 3 is illustrated. As shown in the cross-sectional view, the bioindicator component 20 includes the attachment mechanism 40, i.e. the hooks 42, along a bottom end 44, which are attached to the composite fabric 22. The bioindicator material 26 is provided above the composite fabric 22, but within the interior cavity 30 formed by the membrane 24. In alternative embodiments, additional layers are included, however, it may be desirable to limit the number of layers so as to reduce a size of the bioindicator component 20 as it may be worn on clothing, shoes, hats, etc.

Figure 5:
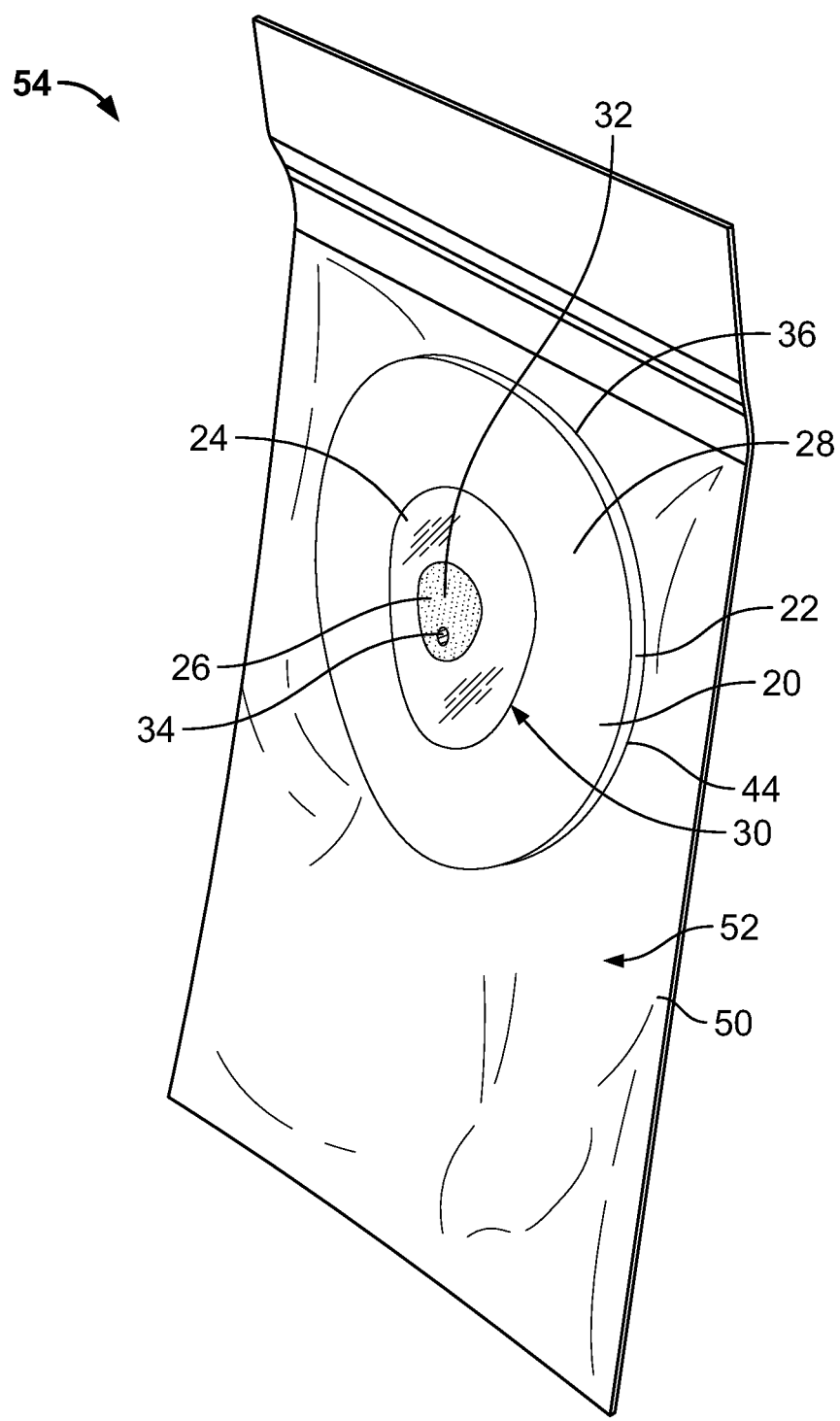
FIG. 5 is an isometric view of the bioindicator component of FIG. 1 in a re-sealable pouch.

Referring to FIG. 5, an isometric view of the bioindicator component 20 is shown in a pouch 50. The pouch 50 may be re-sealable, or may be sealable using a mechanism not specifically referenced herein. However, in a preferred embodiment, the pouch 50 may be closed around the bioindicator component 20 so as to prevent gas from entering into a pouch cavity 52 defined by the pouch 50. As noted above, when the bioindicator component 20 is not in use, a wearer may place the bioindicator component 20 back into the re-sealable pouch 50 to prevent the bioindicator component 20 from interacting with the outside environment 54. In some embodiments, the bioindicator component 20 may "recharge" by being placed into the re-sealable pouch 50, such that the bioindicator component 20 returns to a non-affected color, shape, form, or texture, i.e., a null state. Once the bioindicator component 20 is removed from the re-sealable pouch 50, the bioindicator component 20 may change to another color, shape, form, or texture, as discussed in greater detail hereinafter below.

Figures 6A, 6B, 6C:
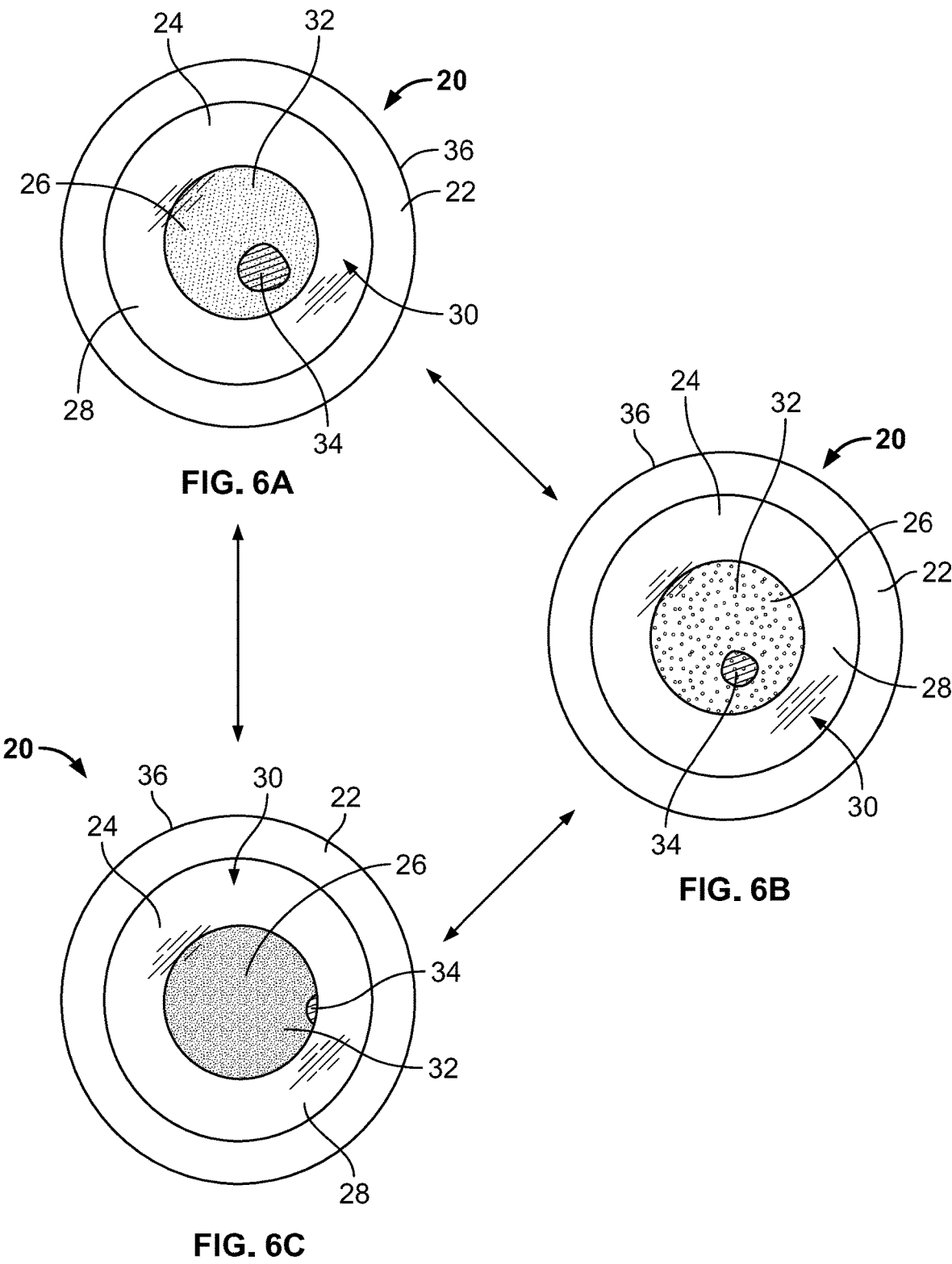
FIGS. 6A-6C are schematic views of the bioindicator component of FIG. 1 transitioning from a first state to a second state to a third state.

FIGS. 6A-6C illustrate schematic views of the bioindicator component 20 transitioning from a first or null state to a second state to a third state. The below description of differing states is for informational purposes only, and is not intended to be limiting. Further, additional states are contemplated, such that the bioindicator component 20 may present different colors, forms, shapes, or textures between four, five, six, seven, eight or more different states. Referring specifically to FIG. 6A, the bioindicator component 20 is shown in a first state, which may be when the bioindicator component 20 is inside of, or has just been removed from the re-sealable pouch 50. Referring to FIG. 6B, the bioindicator component 20 is shown in a second state, which may be when the bioindicator component 20 has been subjected to a first outer environment, which may be defined by a first level of $CO_2$ or another type of stimulant. Further, in some embodiments, the second state may be achieved nearly instantaneously after the bioindicator component 20 has been removed from the pouch 50. Referring to FIG. 6C, the bioindicator component 20 is shown in a third state, which may be achieved after prolonged exposure of the bioindicator component 20 to the ambient atmosphere, or may be achieved when the bioindicator component 20 has been subjected to a second outer environment, which may be defined by a second level of $CO_2$ or another type of stimulant. The bioindicator component 20 may be returned to the first state by returning the bioindicator component 20 to the re-sealable pouch for an identified amount of time, for example, 60 minutes.

Figures 7A, 7B, 7C:
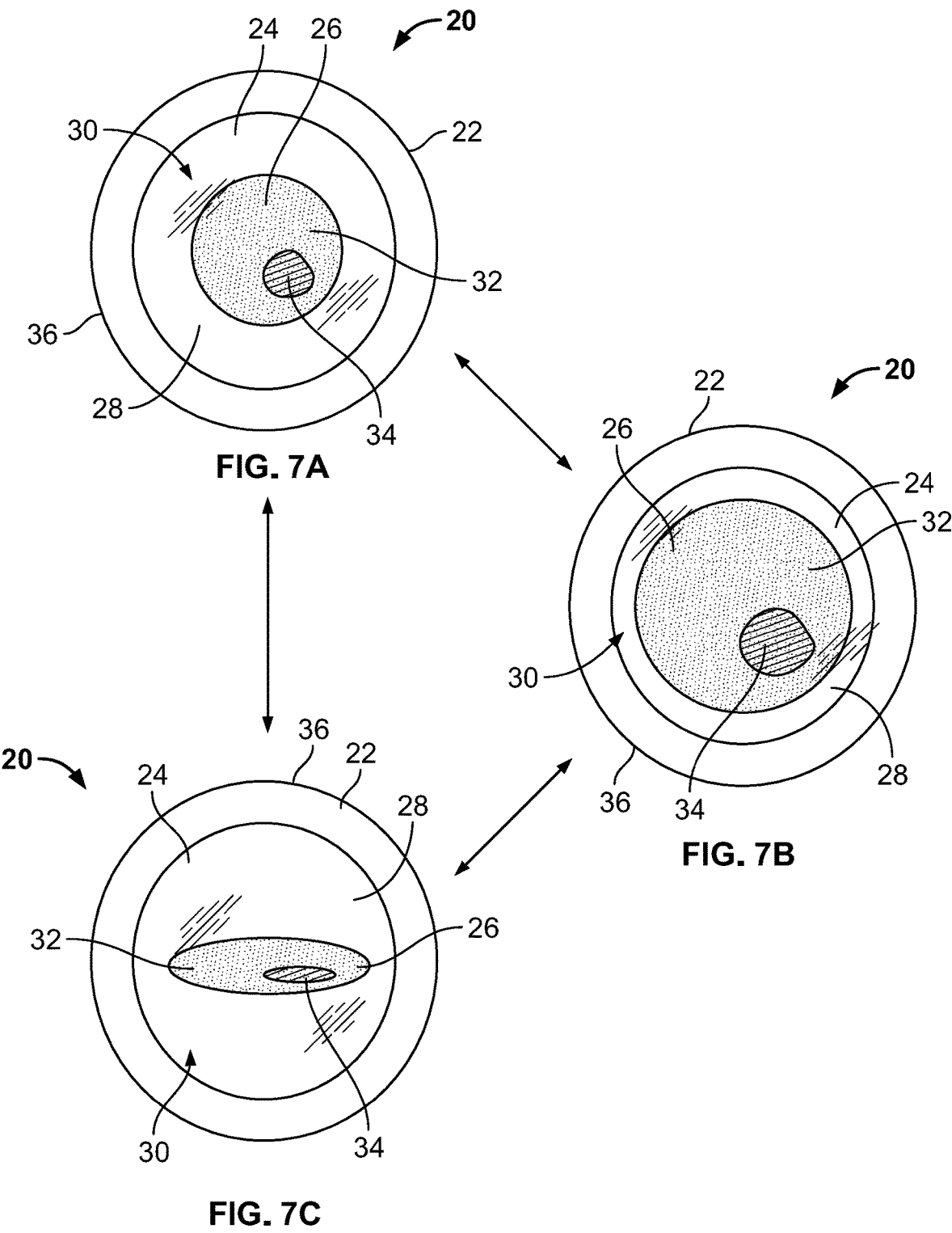
FIGS. 7A-7C are additional schematic views of the bioindicator component of FIG. 1 transitioning from a first state to a second state to a third state.

The differing states shown between FIGS. 6A-6C generally illustrate that the bioindicator component 20 transitions from a first color to a second color to a third color. As noted above, additional changes in color are contemplated, such that there is a fourth state, a fifth state, a sixth state, etc. However, the bioindicator component 20 need not change color, but rather may change form. FIGS. 7A-7C illustrate additional schematic views of the bioindicator component 20 transitioning from a first state to a second state to a third state. FIG. 7A illustrates the bioindicator component 20 in a first state, for example, which may be realized once the bioindicator component 20 has been removed from the re-sealable pouch 50. FIG. 7B illustrates the bioindicator component 20 in a second state, where the bioindicator material 26 has grown from a first size to a second size that is larger than the first size. FIG. 7C shows the bioindicator component 20 in a third state, where the bioindicator material 26 has shrunk from the second size to a third size smaller than the second size. Once the bioindicator component 20 has been placed back into the re-sealable pouch 50, the bioindicator component 20 may transition back to the first size, as shown in FIG. 7A. While the size differentials noted above are non-limiting examples of how the bioindicator may change shape, any number of varying size/shape transitions are contemplated between first, second, and third states. Further, additional states are contemplated.

Figure 8:
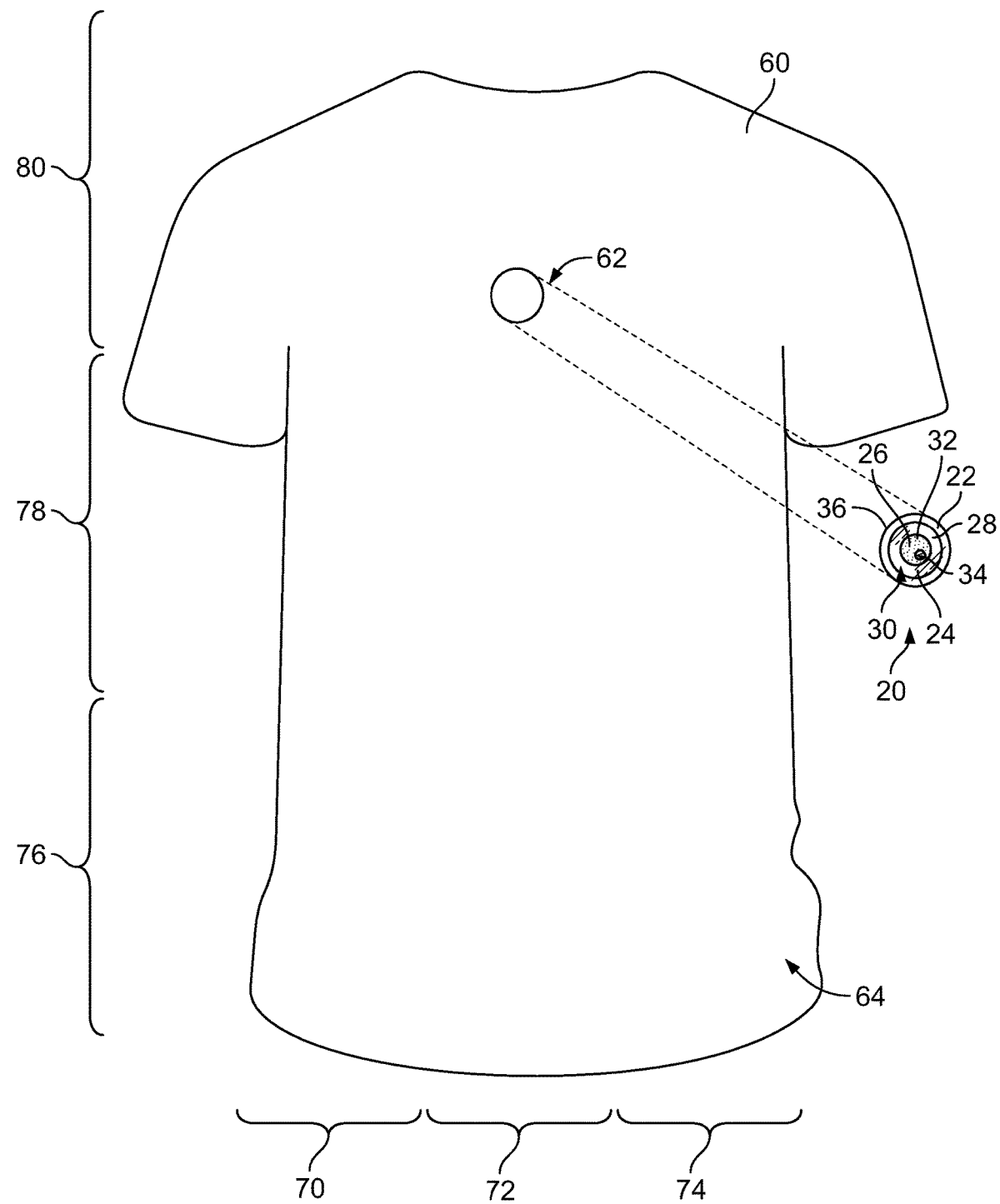
FIG. 8 is a front view of the bioindicator component of FIG. 1 shown separated from a t-shirt.

Referring to FIG. 8, a detailed front view of the bioindicator component 20 is shown exploded from an article, i.e., an article of clothing 60, which in the present embodiment is a t-shirt. The bioindicator component 20 is shown separated from the article of clothing 60, however, a placement location 62 along a front 64 of the article of clothing 60 is clearly shown. The bioindicator component 20 may be placed along any portion of the article of clothing 60, however, it is advantageous to centrally locate the bioindicator component 20 along the front 64 of the article of clothing 60 so that a wearer can easily view and access the bioindicator component 20. In that sense, the article of clothing 60 may be defined as having a left portion 70, a central portion 72, and a right portion 74, along with a lower portion 76, a medial portion 78, and an upper portion 80. The portions 70, 72, 74, 76, 78, 80 may generally comprise equal areas of the article of clothing 60, and are intended to separate the article of clothing 60 into specific regions. In the present embodiment, the bioindicator component 20 is disposed within the central portion 72 and the upper portion 80. The central and upper location of the bioindicator component 20 along the article of clothing 60 may allow a wearer to more easily view the bioindicator component 20 to determine whether the wearer is in an area having high or undesirable levels of a certain type of gas, pollutant, or contaminant. However, the bioindicator component 20 may be disposed within any of the portions 70, 72, 74, 76, 78, 80.

Figure 9:
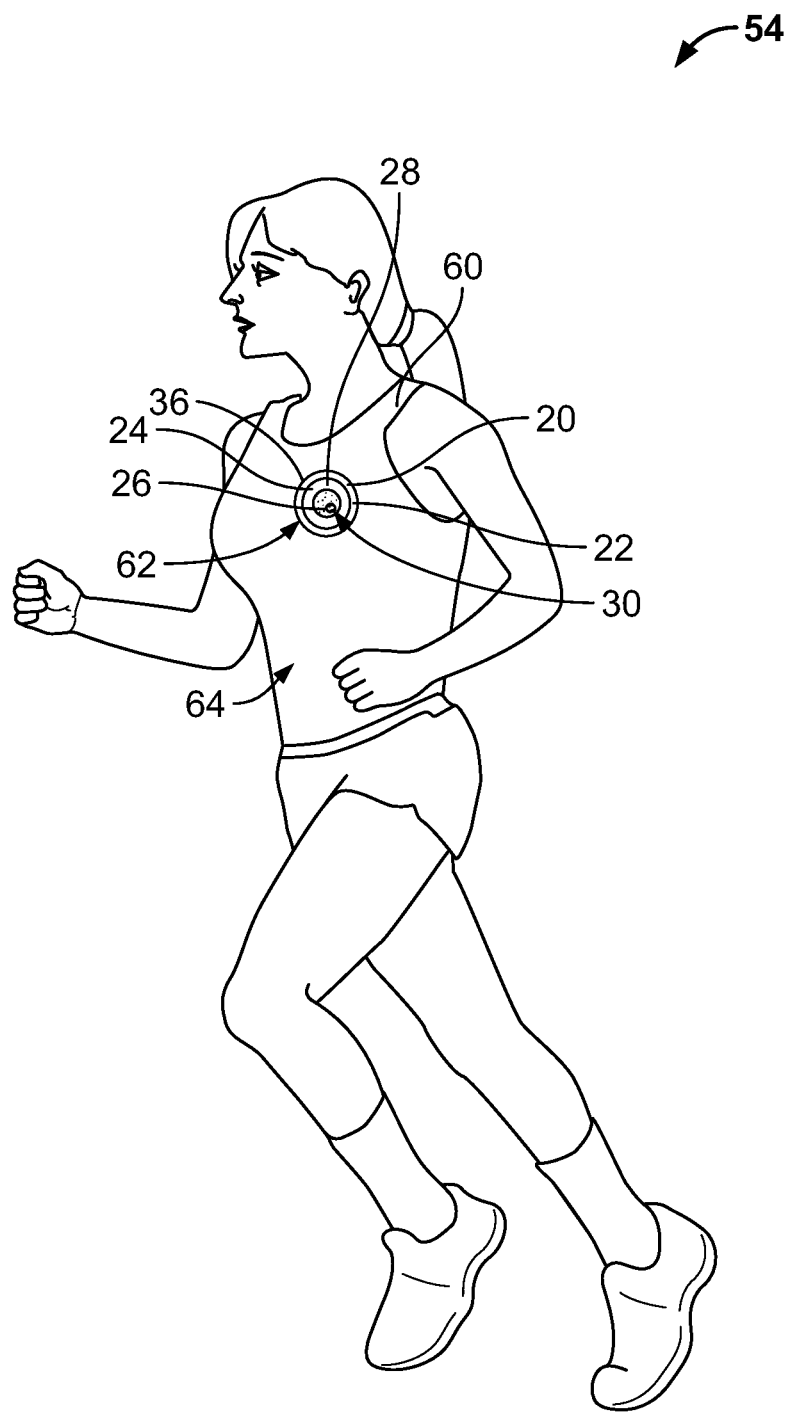
FIG. 9 is an isometric view of a bioindicator component shown on an article of clothing being worn by a wearer.

Now referring to FIG. 9, the bioindicator component 20 is shown on an article of clothing 60 being worn by a person 82. While the bioindicator component 20 is shown being generally located along the left portion 70 and the upper portion 80 of the article of clothing 60 being worn by the person 82 (which is a tank top in the present embodiment), the bioindicator component 20 may be located along other portions of the article of clothing 60. The bioindicator component 20 may be applied to the article of clothing 60 before the person 82 engages in a physical activity, such as running outdoors. The bioindicator component 20 may be helpful to the person 82 so as to provide an indication that the outside environment 54 is safe for physical activity, or may change color, shape, texture, or form so as to indicate to the person 82 that engaging in a physical activity may be undesirable.

Figure 10A:
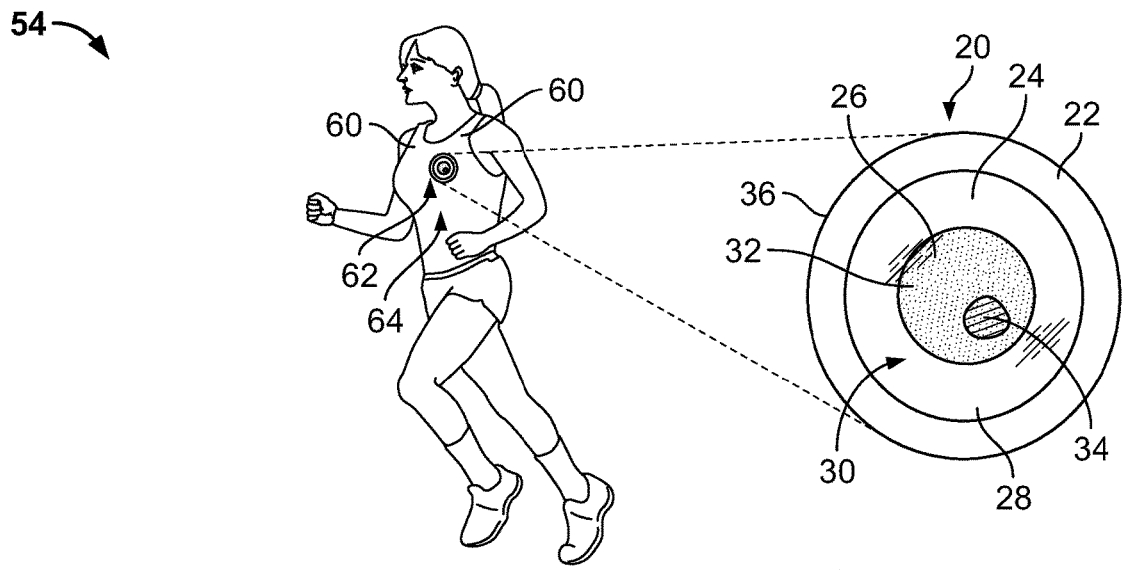
FIGS. 10A-10C are isometric views of the bioindicator component of FIG. 1 shown enlarged along an article of clothing in a first state, a second state or smoggy environment, and a third state or partly sunny environment, respectively.
Figures 10B, 10C:
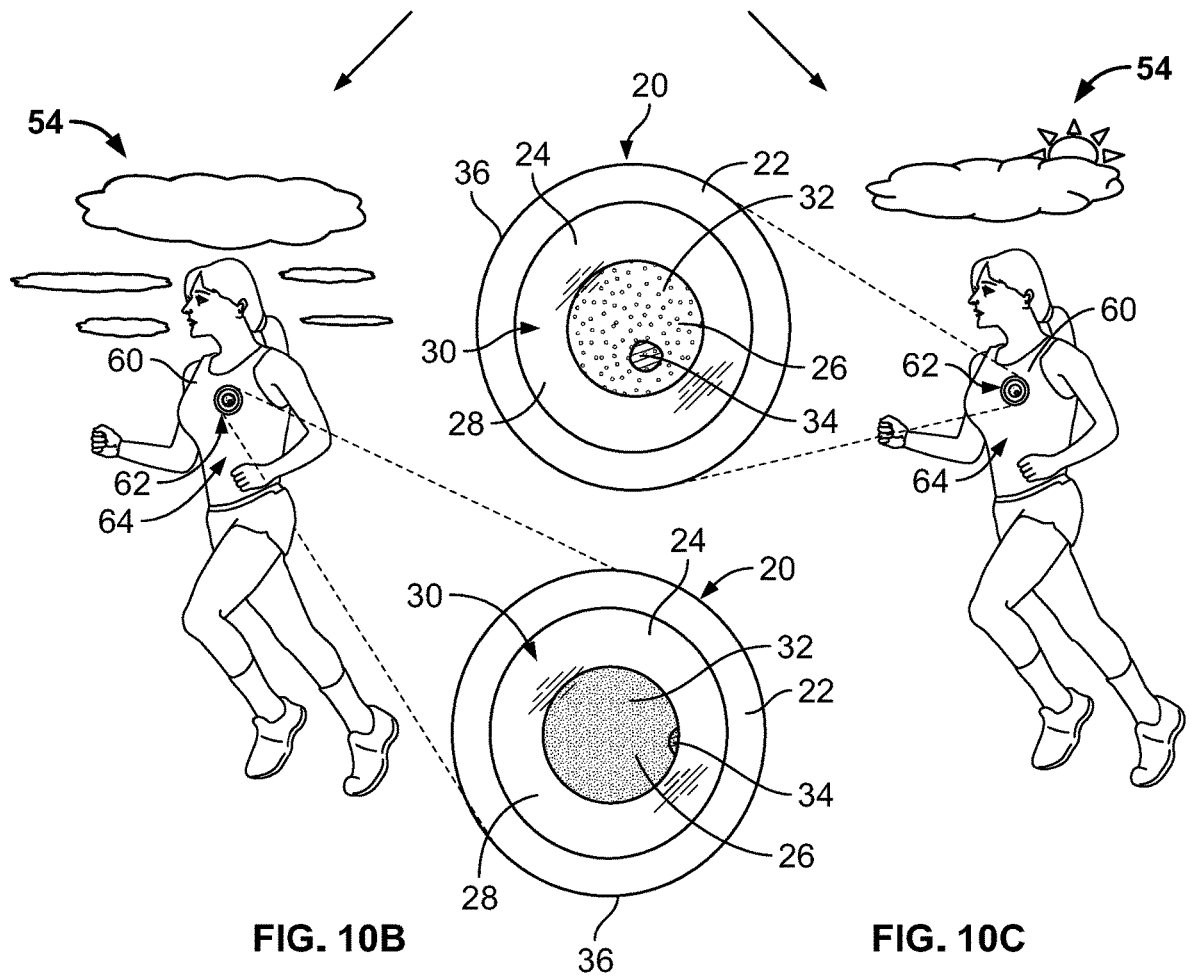

FIGS. 10A-10C illustrate views of the bioindicator component 20 coupled with an article of clothing in a first state, a second state or smoggy environment, and a third state or partly sunny environment, respectively. Referring to FIG. 10A, the bioindicator component 20 is shown along, and exploded from, the article of clothing 60. In FIG. 10A, the bioindicator component 20 is shown immediately after having been removed from the pouch 50, such that the surrounding environment 54 has had a minimal amount of time to affect the color, form, shape, or texture of the bioindicator material 26 therein. FIGS. 10B and 10C illustrate different states into which the bioindicator component 20 may transition, based on the contents of the surrounding environment 54. FIG. 10B illustrates a second state, which may be indicative of a smoggy environment. In the smoggy environment, the bioindicator component 20 may transition into a state having a color, shape, form, or texture indicative of a smoggy environment, which may be based on a level of $CO_2$ in the atmosphere. In some embodiments, a level of $CO_2$ may be used as a proxy to indicate whether other pollutants are present within the surrounding environment, such as ozone or particulate matter. FIG. 10C illustrates a third state, which may be indicative of a sunny or partly sunny environment. In the third state, the bioindicator component 20 may transition into a state having a color, shape, form, or texture indicative of a clean or non-polluted environment.

Figure 11:
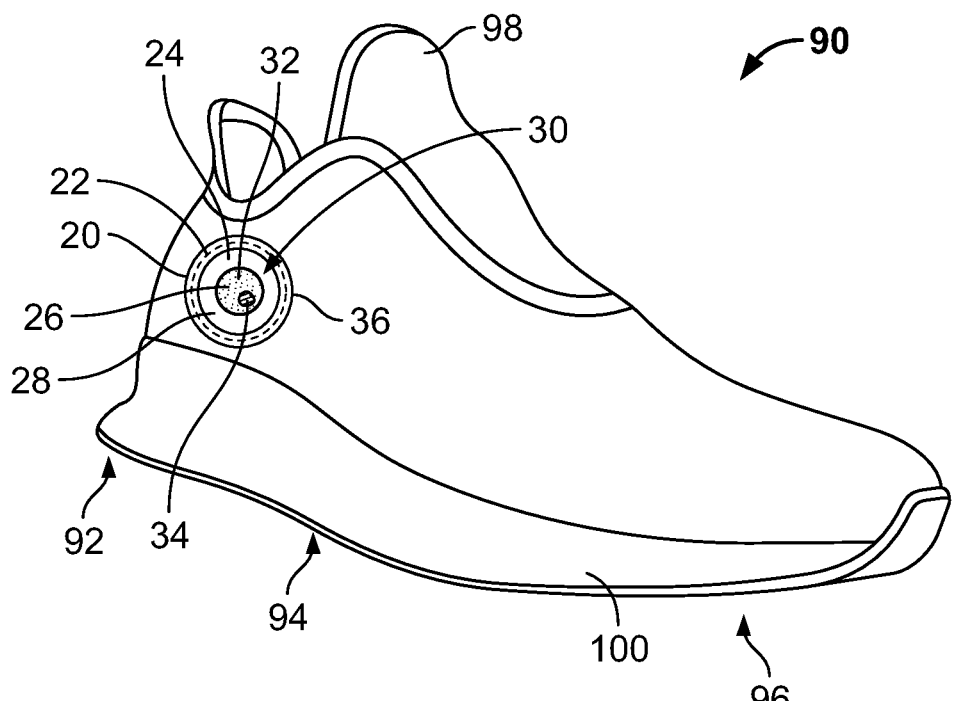
FIG. 11 is an isometric view of the bioindicator component of FIG. 1 shown on an article of footwear.

Referring now to FIG. 11, the bioindicator component 20 is shown applied to an article of footwear 90. In the present embodiment, the bioindicator component 20 is generally in the same form as described above; however, certain aspects of the bioindicator component 20, such as the size, shape, or attachment mechanism 40, may be altered so as to be usable with the article of footwear 90. The article of footwear 90 may be any type of article of footwear 90, and the bioindicator component 20 may be positioned along any portion of the article of footwear 90. In some embodiments, the bioindicator component 20 is positioned along a heel region 92 of the article of footwear 90. However, in some embodiments, the bioindicator component 20 may be positioned along a midfoot region 94, a forefoot region 96, and/or a tongue 98 of the article of footwear 90. In some embodiments, and as discussed below, the bioindicator component 20 may be disposed along a sole structure 100 of the article of footwear 90.

Figure 12:
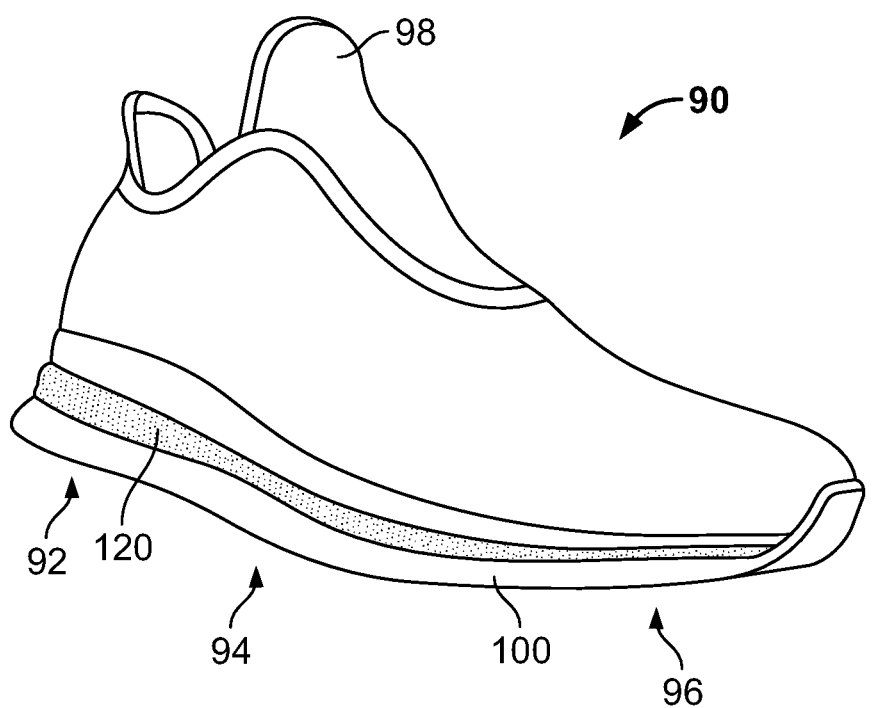
FIG. 12 is an isometric view of another embodiment of a bioindicator component along a sole structure of an article of footwear.

FIG. 12 illustrates a view of another embodiment of a bioindicator component 120 that is disposed along the sole structure 100 of the article of footwear 90. In the present embodiment, the bioindicator component 120 is not circular, but rather extends longitudinally along the sole structure 100. The bioindicator component 120 may be integrally formed with the sole structure 100 of the article of footwear 90, or may be separable therefrom. In some embodiments, the bioindicator component 120 is separable from the sole structure 100 by peeling the bioindicator component 120 off. In that sense, the attachment mechanism (not shown) along an underside of the bioindicator component 120 may be formed to allow for detachment and attachment to and from the sole structure 100.

Figure 13:
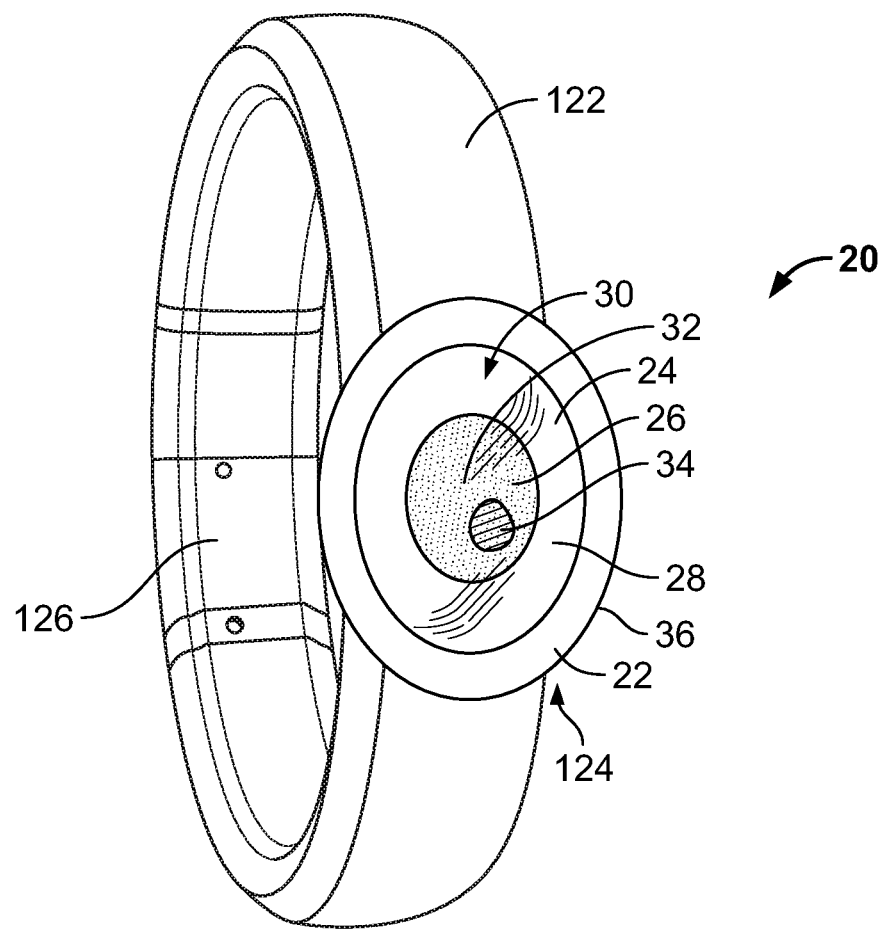
FIG. 13 is an isometric view of yet another embodiment of a bioindicator component disposed along a wristband.

FIG. 13 illustrates yet another embodiment of the bioindicator component 20 disposed along a wristband 122. The bioindicator component 20 may be attachable to and detachable from a pedestal 124 along the wristband 122. In some embodiments, the wristband 122 may comprise components such as a watch head (not shown) or a clasping mechanism 126 that allows the wristband 122 to be removed from the wrist of a user. In some embodiments, the bioindicator component 20 has a smaller profile, but may still maintain the circular shape, similar to the bioindicator component described above. The bioindicator component 20 may be positioned along any portion of the wristband 122.

Figure 14A:
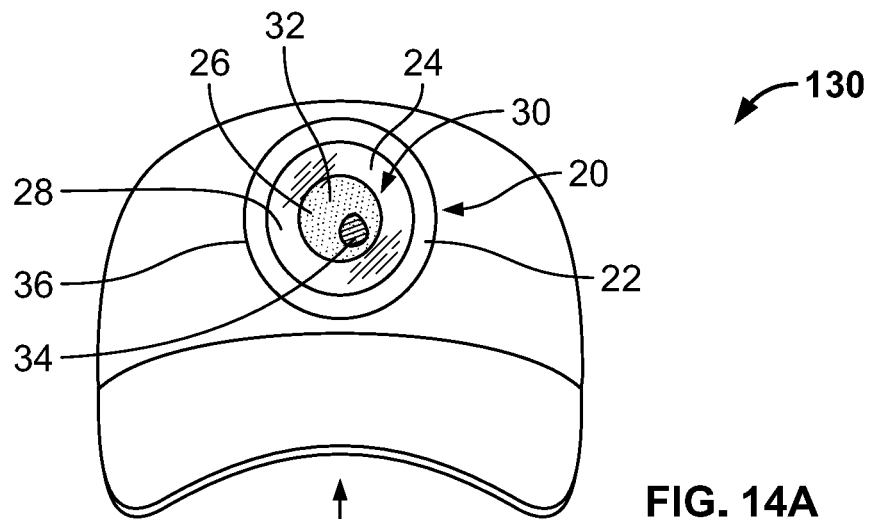
FIGS. 14A-14C are schematic views of a cap or hat having the bioindicator component applied thereto or disposed therealong.
Figure 14B:
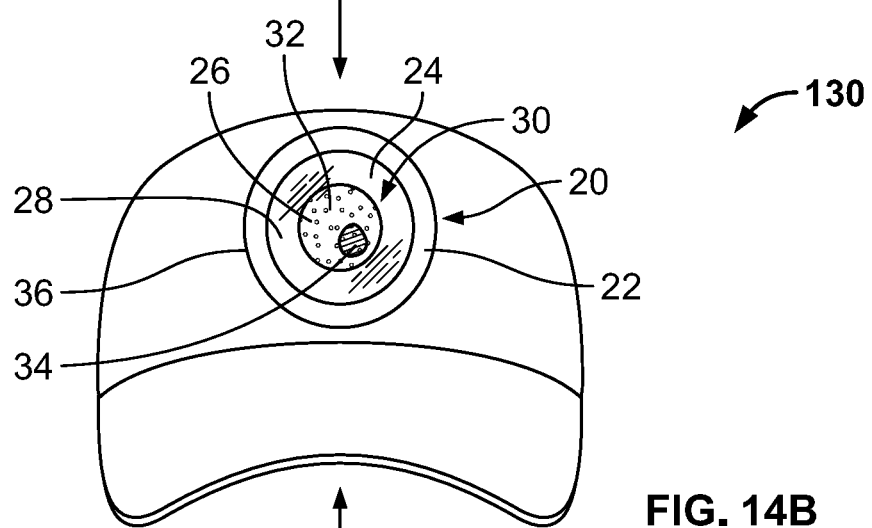
Figure 14C:
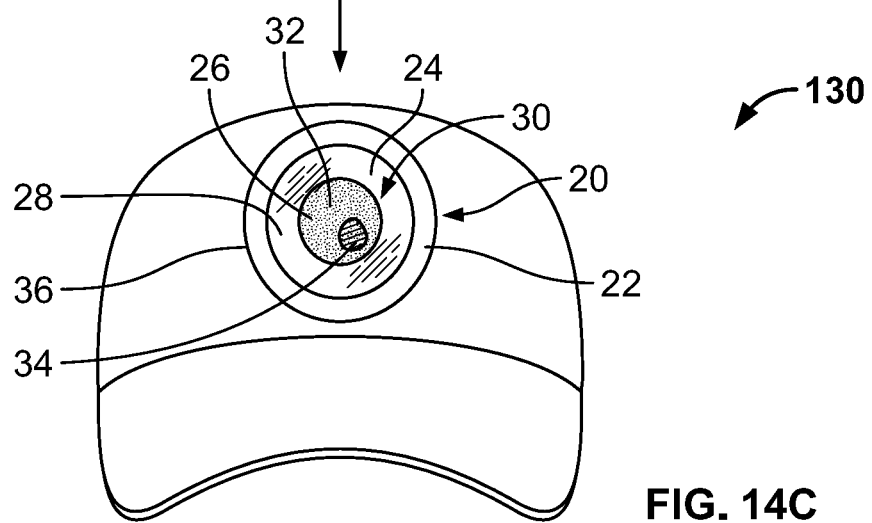

FIGS. 14A-14C illustrate schematic views of a cap or hat 130 having the bioindicator component 20 applied thereto, wherein the bioindicator component 20 transitions from a first or null state to a second state to a third state in a similar fashion as shown with respect to FIGS. 6A-6C. As noted above, additional states are contemplated, such that the bioindicator component 20 may present different colors, forms, shapes, or textures between four, five, six, seven, eight, or more different states. Referring specifically to FIG. 14A, the bioindicator component 20 is shown in a first state, which may be when the bioindicator component 20 is inside of, or has just been removed from the re-sealable pouch 50 and applied to the hat 130. Referring to FIG. 14B, the bioindicator component 20 is shown in a second state, which may occur when the bioindicator component 20 has been subjected to a first outer environment, which may be defined by a first level of $CO_2$ or another type of stimulant. Further, in some embodiments, the second state may be achieved nearly instantaneously after the bioindicator component 20 has been removed from the pouch 50. Referring to FIG. 14C, the bioindicator component 20 is shown in a third state, which may be achieved after prolonged exposure of the bioindicator component 20 to the ambient atmosphere, or may be achieved when the bioindicator component 20 has been subjected to a second outer environment, which may be defined by a second level of $CO_2$ or another type of stimulant. The bioindicator component 20 may be returned to the first state by returning the bioindicator component 20 to the re-sealable pouch for an identified amount of time, for example, 60 minutes.

Figure 15:
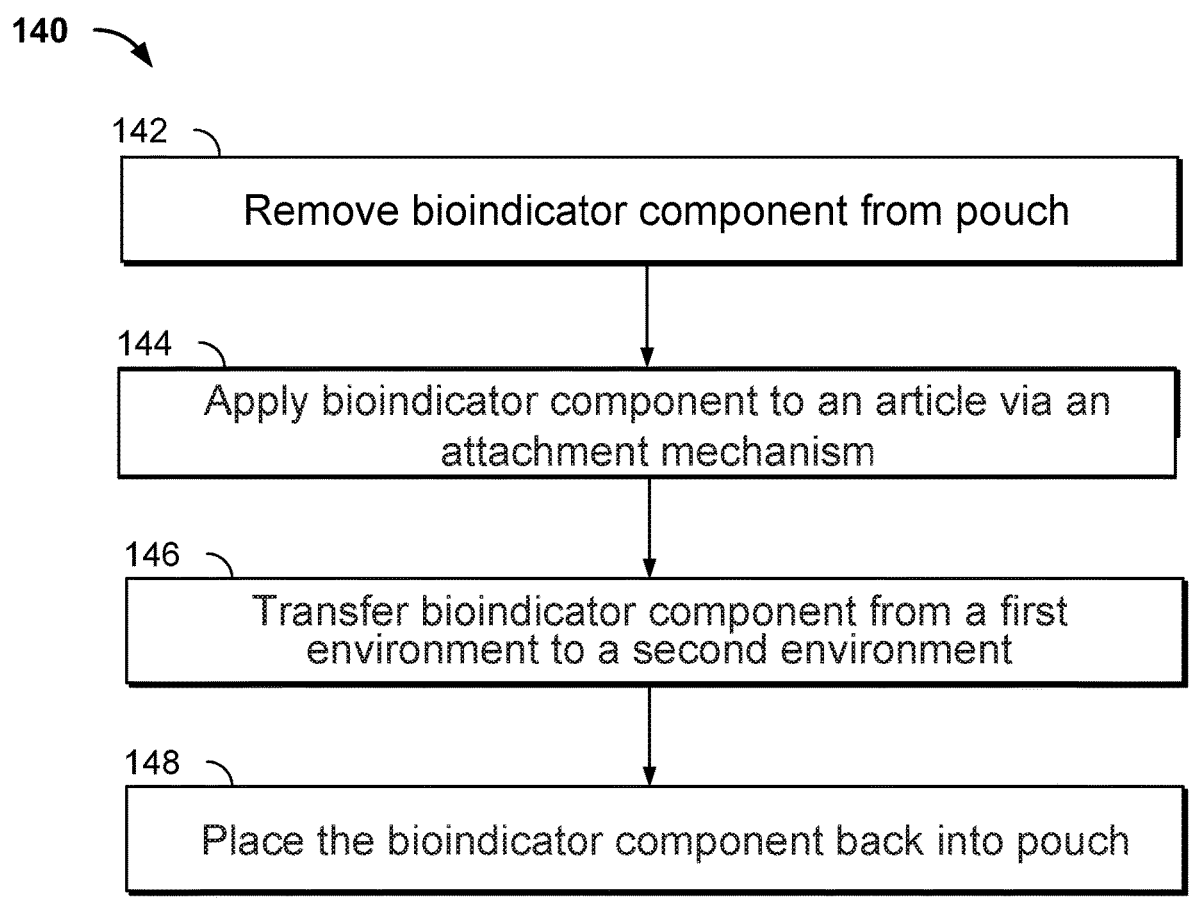
FIG. 15 is a flow chart that provides for a method of using the bioindicator component.

Referring to FIG. 15, a method 140 of using the bioindicator component 20 is depicted through a flow chart. At step 142, the method includes the step of removing the bioindicator component 20 from the pouch 50. At step 144, the method includes the step of applying the bioindicator component to an article, such as the article of clothing 60, via the attachment mechanism 40 along the bioindicator component 20. At step 146, the method 140 further includes the step of transferring the bioindicator component from a first environment to a second environment, wherein a $CO_2$ level is greater in the second environment than the first environment. Finally, at step 148, the method 140 includes the step of placing the bioindicator component 20 back into the pouch 50.

Any of the embodiments described herein may be modified to include any of the structures or methodologies disclosed in connection with different embodiments. Further, the present disclosure is not limited to articles of footwear of the type specifically shown. Still further, aspects of the articles of footwear of any of the embodiments disclosed herein may be modified to work with any type of footwear, apparel, or other athletic equipment.

As noted previously, it will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein. Various features and advantages of the invention are set forth in the following claims.

INDUSTRIAL APPLICABILITY

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

We claim:

1. A bioindicator component for determining a level of $CO_2$ in a surrounding environment, comprising:
   a composite fabric that includes a substrate, wherein a biodegradable material is applied to the substrate;
   a membrane that is coupled with the composite fabric to define an interior cavity, the membrane being semi-permeable;
   a bioindicator that changes color, form, shape, or texture when exposed to $CO_2$; and
   an attachment mechanism coupled to a rear side of the composite fabric.

2. The bioindicator component of claim 1, wherein the substrate is in the shape of a circle.

3. The bioindicator component of claim 2, wherein the attachment mechanism comprises hooks.

4. The bioindicator component of claim 1, wherein the bioindicator changes color when exposed to $CO_2$.

5. The bioindicator component of claim 1, wherein the bioindicator comprises an algae.

6. The bioindicator component of claim 5, wherein the algae is of the type oscillatoria.

7. The bioindicator component of claim 5, wherein when the bioindicator component is exposed to a threshold level of $CO_2$, the bioindicator component turns purple.

8. A bioindicator assembly for determining a level of $CO_2$ in a surrounding environment, comprising:
   an article; and
   a bioindicator component applied to the article, the bioindicator component comprising:
      a composite fabric that includes a substrate, wherein a biodegradable material is applied to the substrate;
      a membrane that is coupled with the composite fabric to define an interior cavity, the membrane being semi-permeable;
      a bioindicator that changes color, form, shape, or texture when exposed to $CO_2$; and
      an attachment mechanism coupled to a side of the composite fabric.

9. The bioindicator component of claim 8, wherein the article is an article of clothing.

10. The bioindicator component of claim 8, wherein the article is an article of footwear.

11. The bioindicator component of claim 8, wherein the bioindicator comprises an algae that changes color when exposed to $CO_2$.

12. The bioindicator component of claim 11, wherein the algae is of the type oscillatoria.

13. The bioindicator component of claim 12, wherein when the bioindicator component is exposed to a threshold level of $CO_2$, the bioindicator component turns a different color.

14. A method of utilizing a bioindicator assembly that can determine a threshold level of $CO_2$ in a surrounding environment, comprising:
  removing a bioindicator component from a pouch, the bioindicator component comprising:
    a composite fabric that includes a substrate, wherein a biodegradable material is applied to the substrate,
    a membrane that is coupled with the composite fabric to define an interior cavity, the membrane being semi-permeable,
    a bioindicator that changes color, form, shape, or texture when exposed to $CO_2$, and
    an attachment mechanism coupled to a rear side of the composite fabric;
  applying the bioindicator component to an article via the attachment mechanism along the bioindicator component.

15. The method of claim 14, wherein the article is an article of clothing.

16. The method of claim 14, wherein the article is an article of footwear.

17. The method of claim 14, wherein the bioindicator comprises an algae that changes color when exposed to $CO_2$.

18. The method of claim 17, wherein the algae is of the type oscillatoria.

19. The method of claim 14, wherein when the bioindicator component is exposed to a threshold level of $CO_2$, the bioindicator component turns a different color.

20. The bioindicator of claim 14, wherein the attachment mechanism comprises a hook and loop structure.

* * * * *